(12) United States Patent
Song et al.

(10) Patent No.: US 7,642,381 B2
(45) Date of Patent: Jan. 5, 2010

(54) TWO STEP PROCESS FOR PREPARING SUBSTITUTED ANISIDINES

(75) Inventors: Jinhua J. Song, Hopewell Junction, NY (US); Jinghua Xu, Danbury, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 12/160,454

(22) PCT Filed: Jan. 18, 2007

(86) PCT No.: PCT/US2007/060674

§ 371 (c)(1),
(2), (4) Date: Jul. 10, 2008

(87) PCT Pub. No.: WO2007/130704

PCT Pub. Date: Nov. 15, 2007

(65) Prior Publication Data

US 2008/0312473 A1      Dec. 18, 2008

Related U.S. Application Data

(60) Provisional application No. 60/743,168, filed on Jan. 25, 2006.

(51) Int. Cl.
*C07C 213/08*      (2006.01)
*C07C 211/40*      (2006.01)
(52) U.S. Cl. .................... 564/443; 564/462
(58) Field of Classification Search ............... 564/443, 564/462
See application file for complete search history.

(56) References Cited

U.S. PATENT DOCUMENTS 4,212,823 A     7/1980  Muller

2005/0020503 A1    1/2005  Llinas-Brunet et al.
2005/0080005 A1    4/2005  Llinas-Brunet et al.

OTHER PUBLICATIONS

Database CAPLUS on STN, Acc. No. 1983:438076, Carter et al., Journal of Fluorine Chemistry (1982), 21(4), p. 407-411 (abstract).*
Eastham et al; The base-catalyzed isomerization of 5,8-dihydro-1-naphthol and its methyl ether; Journal of the American Chemical Society; vol. 80; 1958; pp. 2887-2893.
International Search Report, Form PCT/ISA/210, for corresponding PCT/US2007/060674, (2007).

* cited by examiner

*Primary Examiner*—Brian J Davis
(74) *Attorney, Agent, or Firm*—Michael P. Morris; Mary-Ellen M. Devlin; Philip I. Datlow

(57) ABSTRACT

The process of the present invention can be briefly summarized as depicted in the following scheme: $R_1$ is $C_1$-Calkyl, $R_2$ is $C_1$-$C_6$alkyl and Hal is a halogen atom.

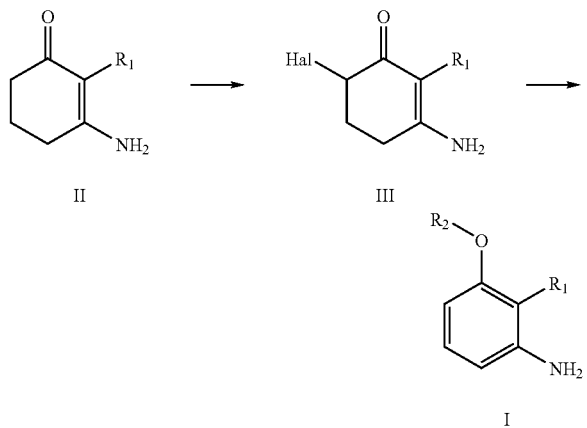

15 Claims, No Drawings

TWO STEP PROCESS FOR PREPARING SUBSTITUTED ANISIDINES

CROSS-REFERENCE TO RELATED APPLICATIONS

This application claims benefit from U.S. Provisional Application No. 60/743,168, filed Jan. 25, 2006.

BACKGROUND OF THE INVENTION

1. Technical Field

The invention relates to an improved process for the preparation of substituted anisidines which are useful as intermediates in the preparation of agents for the treatment of hepatitis C viral (HCV) infections.

2. Background Information

Substituted anisidines of the type described herein have been found to be useful as intermediates in the preparation of certain anti-HCV agents. See, e.g., U.S. Patent Application Publication Nos. US 2005/0020503 A1 and US 2005/0080005 A1, both herein incorporated by reference. However, there is a continuing need to develop an alternative practical and economical synthetic technique for the preparation of these substituted anisidines. The problem addressed by the present invention is to provide a practical and economical process which allows for the efficient manufacture of these compounds with a minimum number of steps.

BRIEF SUMMARY OF THE INVENTION

The substituted anisidines of the present invention are prepared from substituted amino cyclohexenone via aromatization through a halo intermediate. The present invention has the advantage of utilizing relatively inexpensive starting materials and reagents. In addition, the reactions are carried out under simple conditions thus reducing the overall cost. The process of the present invention can be briefly summarized as depicted in the following scheme:

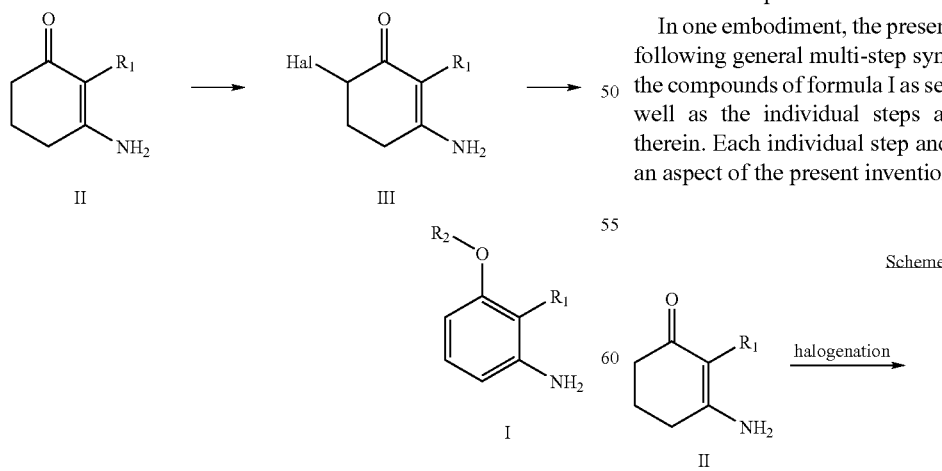

in which $R_1$ is $C_1$-$C_6$alkyl, $R_2$ is $C_1$-$C_6$alkyl and Hal is a halogen atom.

DETAILED DESCRIPTION OF THE INVENTION

Definition of Terms and Conventions Used

The term "alkyl" as used herein, either alone or in combination with another substituent, means acyclic, straight or branched chain alkyl substituents containing the specified number of carbon atoms.

In general, all tautomeric forms and isomeric forms and mixtures, whether individual geometric isomers, stereoisomers, optical isomers or racemic or non-racemic mixtures of isomers, of a chemical structure or compound are intended, unless the specific stereochemistry or isomeric form is specifically indicated in the compound name or structure.

EMBODIMENTS OF THE INVENTION

In the synthetic schemes below, unless specified otherwise, all the substituent groups in the chemical formulas shall have the same meanings as in the general scheme set forth previously. The reactants and reagents used in the synthetic schemes described below may be obtained either as described herein, or if not described herein, are themselves either commercially available or may be prepared from commercially available materials by methods known in the art.

Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by thin layer chromatography or High Pressure Liquid Chromatography (HPLC), if desired, and intermediates and products may be purified by chromatography on silica gel and/or by recrystallization, and characterized by one or more of the following techniques: NMR, mass spectroscopy and melting point.

I. Process Steps

In one embodiment, the present invention is directed to the following general multi-step synthetic method for preparing the compounds of formula I as set forth in Scheme I below, as well as the individual steps and intermediates set forth therein. Each individual step and intermediate is considered an aspect of the present invention.

-continued

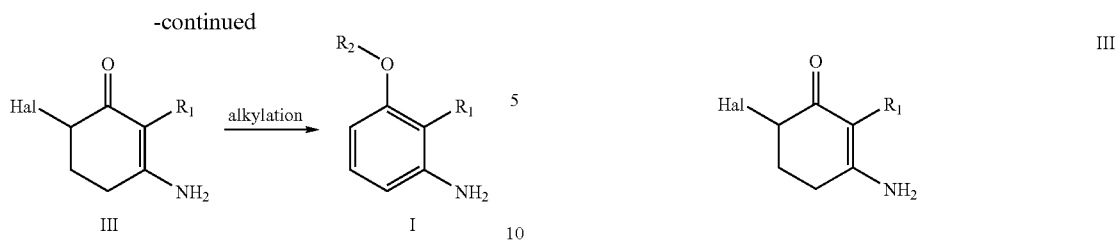

In the first step, an amino ketone compound of formula II, wherein $R_1$ is $C_1$-$C_6$ alkyl is reacted with a halogenating agent in the presence of a base to provide a halogenated amino ketone compound of formula III. Examples of suitable halogenating agents include $I_2$, $Br_2$, iodine monochloride, N-iodosuccinimide, and N-bromosuccinimide; Examples of suitable bases include sodium carbonate, pyridine, amine bases such as TEA, Hunig base, inorganic bases such as $K_2CO_3$, and alkoxide bases such as KOtBu; and examples of suitable solvents for this step include THF, dialkyl ethers such as MTBE, hydrocarbons such as toluene, and heptane. This first step is preferably run at a temperature in the range from −30° C. to 60° C., more preferably in the range from −30° C. to 25° C. The starting materials of Formula II may be obtained by procedures well known in the art, e.g., see Uozumi, et al., Journal of the Chemical Society, Chemical Communications (1991), (2), pgs. 81-3 and Baraldi, et al., Synthesis (1983), (11), pgs 902-3.

In the second step, the ketone of formula III is reacted with an alkylating agent in the presence of a base to provide the desired compound of formula I. Examples of suitable alkylating agents include compounds of the formula $R_2LG$, wherein $R_2$ is $C_1$-$C_6$alkyl and LG is a halide, sulfonate or sulfate, such as $Me_2SO_4$, MeI, MeBr, and $Me_2CO_3$; Examples of suitable bases include pyridine, amine bases such as TEA, Hunig base, inorganic bases such as $K_2CO_3$, and alkoxide bases such as KOtBu; and examples of suitable solvents for this step include THF, methyl THF and diallyl ethers such as MTBE. This second step is preferably run at a temperature in the range from −30° C. to 100° C., more preferably in the range from −20° C. to 40° C.

II. Preferred $R_1$ and $R_2$ Groups

Preferred $R_1$ and $R_2$ groups in the compounds of formulas II, III and I include:

(A) Preferred Definitions of $R_1$:
(i) $R_1$ is $C_{1-3}$ alkyl
(ii) $R_1$ is $C_{1-2}$ alkyl
(iii) $R_1$ is methyl (B) Preferred Definitions of $R_2$:
(i) $R_2$ is $C_{1-3}$ alkyl
(ii) $R_2$ is $C_{1-2}$ alkyl
(iii) $R_2$ is methyl Additional Embodiments are wherein:
(i) $R_1$ is $C_{1-3}$ alkyl and $R_2$ is $C_{1-3}$ alkyl;
(ii) $R_1$ is $C_{1-2}$ alkyl and $R_2$ is $C_{1-2}$ alkyl; or
(iii) $R_1$ is methyl and $R_2$ is methyl.

III. Intermediate of Formula III

In another embodiment, the present invention is directed to the intermediate compound of formula III:

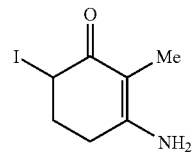

wherein $R_1$ is $C_1$-$C_6$ alkyl and Hal is a halogen atom.

Preferred Embodiments of Formula III (A) Preferred Definitions of $R_1$:
(i) $R_1$ is $C_{1-3}$ alkyl
(ii) $R_1$ is $C_{1-2}$ alkyl
(iii) $R_1$ is methyl (B) Preferred Definitions of Hal:
(i) Hal is bromo, chloro or iodo
(ii) Hal is bromo or iodo
(iii) Hal is iodo.

Another embodiment is directed to intermediates of formula III, wherein $R_1$ is $C_{1-3}$ alkyl, and Hal is bromo, chloro or iodo. Another embodiment is directed to intermediates of formula III, wherein $R_1$ is $C_{1-2}$ alkyl and Hal is bromo or iodo; Another embodiment is directed to intermediates of formula III, wherein $R_1$ is methyl and Hal is iodo, ie. the following compound:

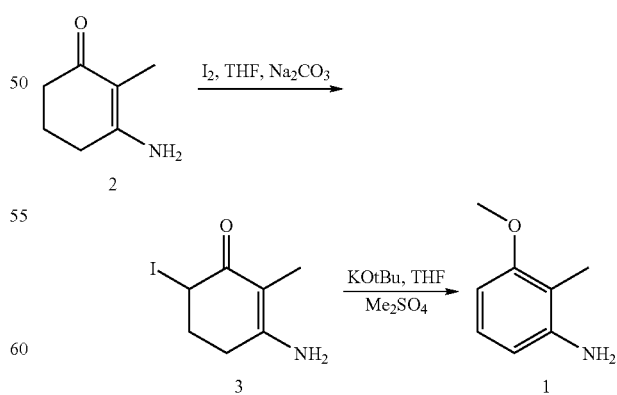

A specific embodiment of the invention is further described by the following non-limiting synthetic examples.

SYNTHETIC EXAMPLE

Synthesis of 3-methoxy-2-methyl aniline 50 g (0.4 mol, 1 eq) of 3-amino-2-methyl-2-cyclohexen-1-one and 106 g (1 ml, 2.5 eq) of sodium carbonate are dispensed into the reactor. 480 mL of MeOH is added. The mixture is cooled in an ice bath to 10° C. A solution of iodine in THF, made by dissolving 253 g (1 mol, 2.5 eq) of iodine in 300 ml of THF, is added to above suspension slowly so that the temperature does not exceed 25° C. The resulting dark suspension is stirred for ~1 h at room temperature and HPLC shows the ending point of reaction (product area percentage at 265 nm was larger than 70%). To the reaction mixture in the ice bath, is added an aqueous saturated solution of sodium sulfite slowly, until the peroxide level is below 3 ppm (by peroxide test strips), and at same time, the sulfite level is below 50 ppm (by sulfite test strips). Approximately 1.5 q of sodium sulfite is used. The suspension is filtered through a celite pad and the pad is washed with 150 mL×3 of THF (washings not optimized). The combined filtrate and washes are concentrated under vacuum until solid crashes out. 250 mL of MTBE is added and the two layer mixture is concentrated again under vacuum until all upper layer evaporates. 250 mL of MTBE and 100 mL of H₂O are added and the mixture is stirred at room temperature for 30 minutes. A dark yellow solid crashes out upon stirring and is filtered and washed with water to give 3-amino-6-iodo-2-methyl-2-cyclohexen-1-one 65 g (65% yield).

2.24 g (20 mmol, 2 eq) of potassium tert-butoxide is dissolved in 60 ml of anhydrous THF and the resulting solution is cooled to −15° C. with stirring. A solution of 2.51 g (10 mmol, 1 eq) of 3-amino-6-iodo-2-methyl-2-cyclohexen-1-one in 25 ml anhydrous THF is added to the potassium tert-butoxide solution and the temperature is kept below −5° C. during addition. The cooling bath is removed after addition and the reaction is allowed to warm up to 5° C. within 1 hour. HPLC shows complete elimination. 1.20 g (9.5 mmol, 0.95 eq) of dimethyl sulfate is added to the reaction mixture with vigorous Stirring. The reaction is shown to be complete by HPLC (~2 h). Then an HPLC weight assay indicates an 89% yield of the product. The isolation of the product was not optimized.

We claim:

1. A process for preparing a compound of formula I, comprising reacting a compound of formula III, wherein Hal is a halogen atom and $R_1$ is $C_1$-$C_6$ alkyl, with an alkylating agent in the presence of a base, to obtain the compound of formula I, wherein $R_1$ is $C_1$-$C_6$ alkyl and $R_2$ is $C_1$-$C_6$ alkyl:

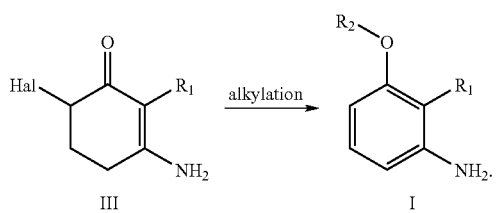

2. A process according to claim 1, wherein the alkylating agent is a compound of the formula $R_2LG$, wherein $R_2$ is $C_1$-$C_6$alkyl and LG is a halide, sulfonate or sulfate.

3. A process according to claim 1, wherein the compound of formula III is prepared by a process comprising reacting a compound of formula II, wherein $R_1$ is $C_1$-$C_6$ alkyl, with a halogenating agent in the presence of a base, to obtain a compound of formula III wherein Hal is a halogen atom and $R_1$ is $C_1$-$C_6$ alkyl:

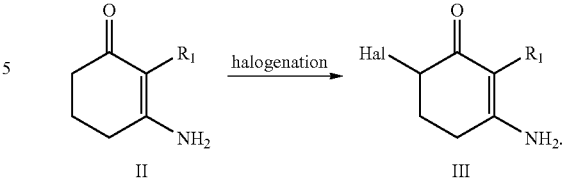

4. A process according to claim 3, wherein the halogenating agent is selected from $I_2$, $Br_2$, iodine monochloride, N-iodosuccinimide, and N-bromosuccinimide.

5. A process according to claim 1, wherein $R_1$ is $C_{1-3}$ alkyl and $R_2$ is $C_{1-3}$ alkyl.

6. A process according to claim 1, wherein $R_1$ is $C_{1-2}$ alkyl and $R_2$ is $C_{1-2}$ alkyl.

7. A process according to claim 1, wherein $R_1$ is methyl and $R_2$ is methyl.

8. A process according to claim 1, wherein Hal is bromo or iodo.

9. A process according to claim 1, wherein Hal is iodo.

10. A compound of the following formula III:

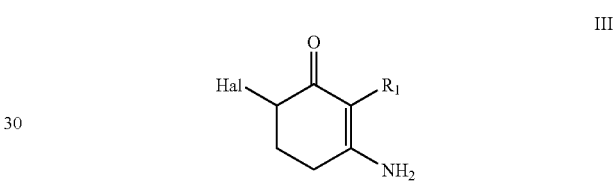

wherein $R_1$ is $C_1$-$C_6$ alkyl and Hal is a halogen atom.

11. A compound of formula III according to claim 10, wherein $R_1$ is $C_{1-3}$ alkyl, and Hal is bromo, chloro or iodo.

12. A compound of formula III according to claim 10, wherein $R_1$ is $C_{1-2}$ alkyl and Hal is bromo or iodo.

13. A compound of formula III according to claim 10, wherein $R_1$ is methyl and Hal is iodo.

14. A process for preparing a compound of formula III according to claim 10, said process comprising reacting a compound of formula II, wherein $R_1$ is $C_1$-$C_6$ alkyl, with a halogenating agent in the presence of a base, to obtain a compound of formula III wherein Hal is a halogen atom and $R_1$ is $C_1$-$C_6$ alkyl:

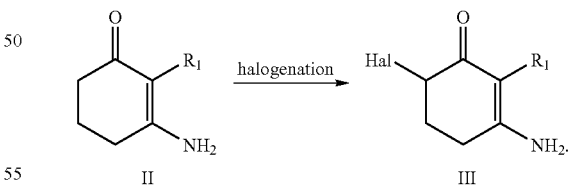

15. A process according to claim 14, wherein the halogenating agent is selected from $I_2$, $Br_2$, iodine monochloride, N-iodosuccinimide, and N-bromosuccinimide.

* * * * *